US006908749B2

(12) United States Patent
Nouchi et al.

(10) Patent No.: US 6,908,749 B2
(45) Date of Patent: Jun. 21, 2005

(54) METHOD FOR PREPARING HUMAN SERUM ALBUMIN CONTAINING HEAT-TREATMENT

(75) Inventors: Toshinobu Nouchi, Kumamoto (JP); Hiroshi Mizokami, Kumamoto (JP); Yoshitaka Tajima, Kumamoto (JP); Yoshinobu Miyatsu, Kumamoto (JP); Masahiro Sakaguchi, Kumamoto (JP); Kazunari Yagi, Kumamoto (JP)

(73) Assignee: Juridical Foundation The Chemo-Sero-Therapeutic Research Institute, Kumamoto (JP)

( * ) Notice: Subject to any disclaimer, the term of this patent is extended or adjusted under 35 U.S.C. 154(b) by 4 days.

(21) Appl. No.: 10/175,103

(22) Filed: Jun. 20, 2002

(65) Prior Publication Data

US 2002/0182680 A1 Dec. 5, 2002

Related U.S. Application Data

(63) Continuation of application No. PCT/JP01/09336, filed on Oct. 24, 2001.

(30) Foreign Application Priority Data

Oct. 24, 2000 (JP) ........................................ 2000-324030

(51) Int. Cl.[7] .................... C07K 14/765; C12P 21/06
(52) U.S. Cl. .................................... 435/69.1; 530/363
(58) Field of Search ............................. 530/363, 364, 530/350, 412; 435/69.1, 7; 514/12

(56) References Cited

U.S. PATENT DOCUMENTS

| 4,025,500 A | * | 5/1977 | Garcia et al. ............... 530/364 |
| 5,132,404 A | * | 7/1992 | Ohtani et al. ............... 530/364 |
| 5,986,062 A | * | 11/1999 | Ohmura et al. ............. 530/363 |

FOREIGN PATENT DOCUMENTS

| EP | 0 073 646 A2 | 9/1983 |
| EP | 0 428 758 A1 | 6/1990 |
| EP | 0 570 916 A2 | 11/1993 |
| JP | 50-71897 | 6/1975 |
| JP | 02-111728 | 4/1990 |
| JP | 3-17023 | 1/1991 |
| JP | 6-71434 | 9/1994 |
| JP | 07-126182 | 5/1995 |
| JP | 08-116985 | 5/1996 |
| JP | 29-26722 | 5/1999 |
| JP | 11-509525 | 8/1999 |

OTHER PUBLICATIONS

J.F. Hansen, et al., A New High Quality Albumin for Therapeutic Use, Joint WHO/IABS Symposium on the Standardization of Albumin, Plasma Substitutes and Plasma–pheresis, Geneva 1980, Develop. Biol. Standard, 48, pp. 105–112 (XP–001079403).

J.T. Edsall, Stabilization of Serum Albumin to Heat, and Inactivation of the Hepatitis Virus, Milestones in Blood Transfusion and Immunohaematology, vol. 46, 1984, pp. 338–340 (XP 000603665).

Alan V. Quirk et al., Production of Recombinant Human Serum Albumin from Saccharomyces Cerevisiae, Biotechnology and Applied Biochemistry, 11, 273–287 (1989).

Ken Okabayashi et al., Secretory Expression of the Human Serum Albumin Gene in the Yeast Saccharomyces Cerevisiae, J. Biochem., 110, 103–110 (1991).

Richard G. Buckholz et al., Yeast Systems for the Commercial Production of Heterologous Proteins, Biotechnology, vol. 9, Nov. 1991, pp. 1067–1072.

Martine Latta et al., Synthesis and Purification of Mature Human Serum Albumin from E. Coli, Biotechnology, vol.5, Dec. 1987, pp. 1309–1314.

Charles W. Saunders, et al., Secretion of Human Serum Albumin from Bacillus subtilis, Journal of Bacteriology, vol. 169, No. 7, Jul. 1987, p. 2917–2925.

Phillip P. Minghetti et al., Molecular Structure of the Human Albumin Gene is Revealed by Nucleotide Sequence Within q11–22 of Chromosome 4, The Journal of Biological Chemistry, vol. 261, No. 15, May 25, 1986, pp. 6747–6757.

Jan H. Bergloef et al., Chromatographic Preparation and in Vitro Properties of Albumin from Human Plasma, Journal of Applied Biochemistry, vol. 5, 282–292 (1983).

\* cited by examiner

*Primary Examiner*—Jon Weber
*Assistant Examiner*—Sheridan K Snedden
(74) *Attorney, Agent, or Firm*—Oblon, Spivak, McClelland, Maier & Neustadt, P.C.

(57) ABSTRACT

A method for preparing human serum albumin comprises the step of heat-treating a human serum albumin solution containing contaminants at a pH value in the proximity to the isoelectric point of the contaminants.

18 Claims, 1 Drawing Sheet

METHOD FOR PREPARING HUMAN SERUM ALBUMIN CONTAINING HEAT-TREATMENT

"This application is a continuation of PCT/JP01/09336, filed Oct. 24, 2001 and claims foreign priority to JAPAN 2000-324030, filed Oct. 24, 2001."

TECHNICAL FIELD

The present invention relates to a method for preparing human serum albumin. More specifically, the present invention pertains to a method for preparing recombinant human serum albumin (hereunder also referred to as "rHSA") according to the gene recombination technique, which comprises the step of a heat-treatment in the proximity to the isoelectric point of the contaminants (mainly comprising proteins) originated from host cells.

BACKGROUND ART

Human serum albumin (hereunder also referred to as "HSA") is a principal protein component present in the plasma, consists of a single chain polypeptide comprising 585 amino acid residues and has a molecular weight equal to about 66,000 Dalton (see Minghetti, P. P. et al. (1986), Molecular structure of the human albumin gene is revealed by nucleotide sequence within 11–22 of chromosome 4. J. Biol. Chem. 261, pp. 6747–6757). It has been known that the principal roles of HSA are not only to maintain the normal osmotic pressure of the blood, but also to bind with a variety of substances such as calcium ions, fatty acids, bilirubin, tryptophan and drugs possibly present in the blood, thereby playing a role of a carrier for transporting these substances. Purified HSA has been used in, for instance, the postoperative treatment after surgical operations and the treatment of hypoalbuminemia caused due to the loss of albumin such as hemorrhagic shock, burn and nephrotic syndromes.

Conventionally, HSA has been prepared by subjecting the human plasma to the low temperature ethanol-fractionation method of Cone or any method similar thereto to give HSA-containing fractions (HSA is fractionated in the fraction V) and then purifying the fraction through the use of a variety of purification techniques. Moreover, there has recently been developed a method in which the human plasma is not used as a raw material, for instance, a technique for producing human serum albumin using yeast, *Escherichia coli* or *Bacillus subtilis* cells, while making use of the gene recombination technique.

These gene recombination techniques are detailed in (1) Production of recombinant Human Serum Albumin from *Saccharomyces cerevisiae*; Quirk, R. et al. Biotechnology and Applied Biochemistry, 1989, 11: 273–287, (2) Secretory Expression of the Human Serum Albumin Gene in the Yeast, *Saccharomyces cerevisiae*; Ken Okabayashi et al. J. Biochemistry, 1991, 110: 103–110, (3) Yeast Systems for the Commercial Production of Heterologous Proteins; Richard G. Buckholz and Martin A. G. Gleeson, Bio/Technology, 1991, 9: 1067–1072 for the yeast, (4) Construction of DNA sequences and their use for microbial production of proteins, in particular, human serum albumin; Lawn, R. M. European Patent Publication No. 0073646A (1983), (5) Synthesis and Purification of mature human serum albumin from *E. coli*; Latta, L. et al. Biotechnique, 1897, 5: 1309–1314 for the *Escherichia coli* (*E. coli*), (6) Secretion of human serum albumin from *Bacillus subtilis*; Saunders, C. W. et al. J. Bacteriol. 1987, 169: 2917–2925 for the *Bacillus subtilis*.

The methods for purifying the human serum albumin usable herein in general include those currently used in the protein chemistry such as a salting out method, an ultrafiltration method, an isoelectric precipitation method, an electrophoresis method, an ion-exchange chromatography technique, a gel filtration chromatography technique and/or an affinity chromatography technique. Indeed, the human serum albumin-containing fraction includes various kinds of contaminants originated from, for instance, biological tissues, cells and blood and therefore, the human serum albumin has been purified by a complicated combination of the foregoing methods. For instance, Japanese Un-Examined Patent Publication No. Hei 5-317079 discloses such a method for preparing human serum albumin comprising the steps of subjecting culture supernatant of human serum albumin-producing recombinant yeast cells to an ultrafiltration treatment, a heat-treatment, a treatment with an acid and an ultrafiltration treatment, in this order and then subjected to a treatment with a cation-exchanger, a hydrophobic chromatography treatment, a treatment with an anion-exchanger and a salting out treatment.

This preparation method is developed to inhibit any coloration of the resulting human serum albumin by heat-treating the supernatant in the presence of a reducing agent. There have also been reported some methods for preparing human serum albumin including the step of a heat-treatment and there have been recognized that a variety of effects can be expected due to the heat-treatment.

For instance, Japanese Examined Patent Publication No. Hei 6-71434 and Japanese Un-Examined Patent Publication No. Hei 8-116985 disclose that a protease is inactivated by heating a human serum albumin-containing culture supernatant prepared according to the gene recombination at a temperature ranging from 50 to 70° C. for 1 to 5 hours in the presence of acetyl tryptophan or an organic carboxylic acid.

Moreover, Japanese Un-Examined Patent Publication No. Hei 7-126182 discloses that microorganisms as impurities are inactivated by heating a recombinant human serum albumin-containing pharmaceutical preparation at a temperature ranging from 50 to 70° C. for not less than 30 minutes.

DISCLOSURE OF THE INVENTION

However, all of the foregoing heat-treatments incorporated into the methods for preparing human serum albumin do not relate to a method for removing proteins included in the recombinant human serum albumin products as impurities.

Accordingly, it is an object of the present invention to provide a method for effectively removing contaminants present in a human serum albumin preparation.

It is another object of the present invention to provide human serum albumin having a high safety as a medicine.

The inventors of this invention have conducted various studies, while taking into consideration the foregoing technical circumstances, have found that proteinaceous contaminants originated from human serum albumin-producing recombinant yeast cells as host cells can effectively be removed by diluting a culture broth of the host cell, subjecting, in order, the diluted culture broth to a treatment with a cation-exchanger, conversion of multimers of human serum albumin into monomers thereof by an alkali-treatment and an ultrafiltration treatment and then subjecting the resulting rHSA-containing solution to a heat-treatment at a pH value in the proximity to the isoelectric point of the proteinaceous contaminants originated from the host cells and have thus completed the present invention.

The present invention relates to a method for preparing human serum albumin characterized by including the step of heat-treating a contaminants-containing human serum albumin solution at a pH value near the isoelectric point of the contaminants. The present invention also embraces high purity rHSA free of any proteinaceous contaminants and prepared according to the foregoing method. The present invention will hereunder be described in more detail.

BEST MODE FOR CARRYING OUT THE INVENTION

Figure 1:
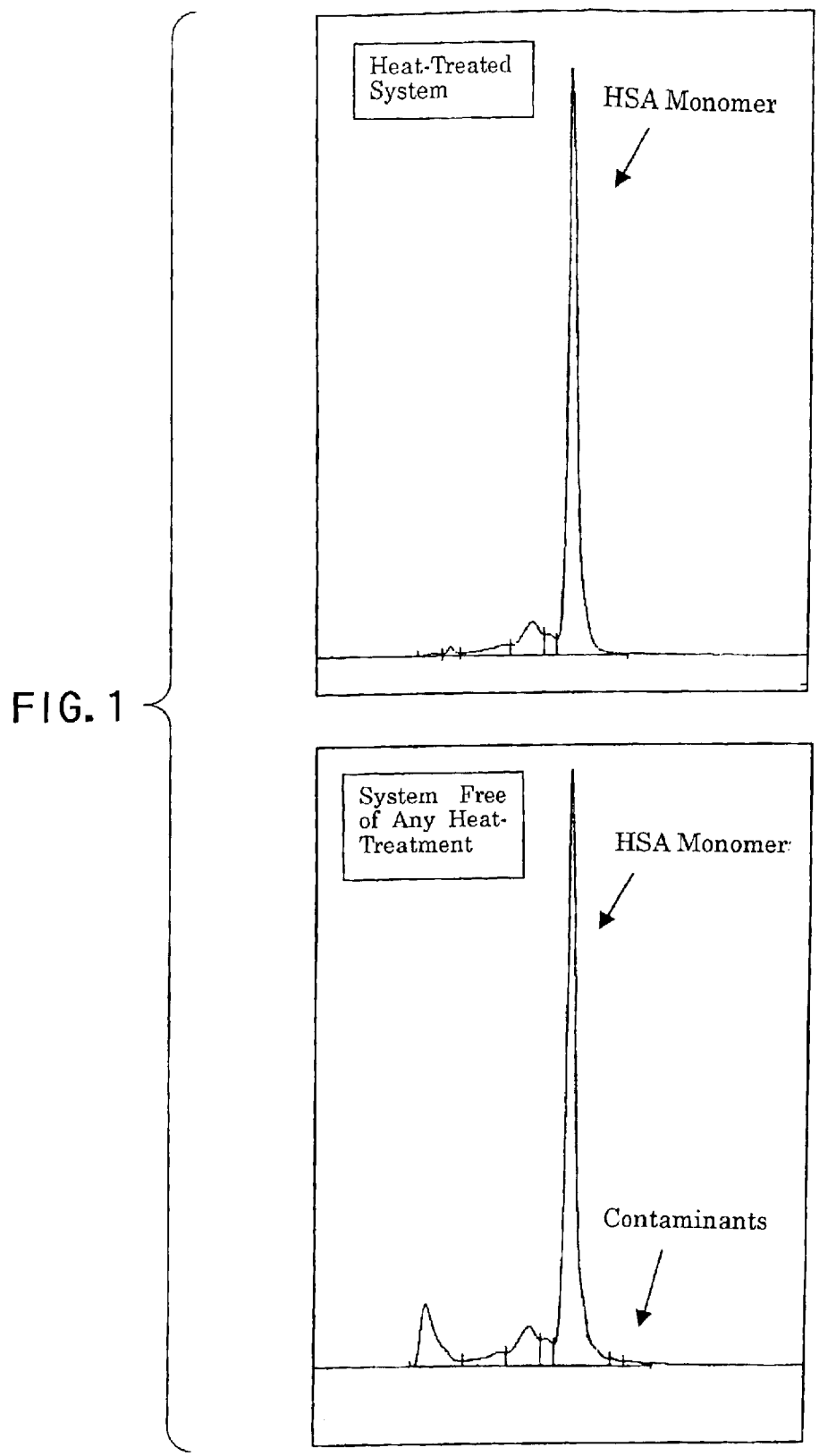
FIG. 1 is a diagram showing the results of gel filtration HPLC analysis of human serum albumin-containing supernatants.

The method of the present invention relates to a method for preparing human serum albumin, wherein a human serum albumin solution containing proteinaceous contaminants originated from host cells is heat-treated at a pH value in the proximity to the isoelectric point of the contaminants originated from the host cells. The practice of this method would permit the easy removal of contaminants originated from, for instance, yeast cells and the preparation of high purity human serum albumin.

The subjects, which may be applied to the heat-treatment of the present invention, may be, for instance, rHSA-containing solutions containing proteinaceous contaminants originated from rHSA-producing host cells and prepared according to the gene recombination technique. Such host cells are not restricted to specific ones and may be, for instance, yeast, *Escherichia coli, Bacillus subtilis* and animal cells. Preferably used herein are yeast cells such as those belonging to the genus *Saccharomyces* and *Pichia*, with *Saccharomyces cerevisiae* AH22 strain or mutants thereof being more preferably used herein. The method of the present invention can be applied not only to the rHSA-containing solution comprising proteinaceous contaminants originated from the rHSA-producing recombinant host cells, but also to a human serum albumin solution containing proteinaceous components originated from the plasma.

The heat-treatment of the present invention can be carried out at any step of the rHSA (or human serum albumin derived from the plasma) production process. For instance, the method of the present invention is desirably applied to the culture supernatant of human serum albumin-producing recombinant yeast cells, crushed yeast cell-containing liquids, rHSA-containing solution obtained by appropriately pre-treating these supernatants or liquids, or those obtained by further purification of the foregoing to some extent through treatments such as ion-exchange, adsorption chromatography, gel filtration and/or salting out treatments. Preferably, the method of the present invention is applied to the culture supernatant of rHSA-producing yeast cells after the supernatant is diluted 2 to 3 times with purified water and then subjected to a treatment with a cation-exchanger, an alkali-treatment and an ultrafiltration treatment.

The treatment with a cation-exchanger is conducted according to the usual method. Examples of cation-exchangers usable herein are sulfo-agarose, sulfo-cellulose, sulfopropyl-agarose, sulfopropyl-dextran, sulfopropyl-polyvinyl, carboxymethyl-agarose, carboxymethyl-dextran and carboxymethyl-cellulose. Either of these carriers may be used in the present invention. For instance, there may be adopted such a method comprising the steps of loading, onto a cation-exchange column equilibrated with a 50 mM acetate buffer (pH 4.5) containing 50 mM sodium chloride, a human serum albumin solution whose pH value is adjusted to that level, washing and then eluting the column with a 50 mM phosphate buffer (pH 9.0) supplemented with 300 mM sodium chloride to give HSA-containing fractions.

Subsequently, the resulting HSA-containing fractions are subjected to an alkali-treatment for converting multimers of human serum albumin generated during cultivation of host cells or human serum albumin-production processes into monomers thereof An alkali solution having a pH value ranging from 8 to 11 and preferably 8.5 to 9.5 is used in the conversion of the multimer into the monomer.

The temperature of the alkali-treatment is not necessarily room temperature and may be one, which never denatures or modifies HSA and rHSA. For instance, the alkali-treatment may be conducted at a temperature ranging from 0 to 65° C., but it is preferred to use a method in which a multimer-containing human serum albumin solution is allowed to stand at room temperature (about 25° C.).

The multimers of human serum albumin is converted into the monomers thereof by mixing a multimer-containing solution with an alkaline solution and then allowing the resulting mixture to stand for at least 15 minutes and preferably not less than 3 hours. There is not any particular upper limit in the time required for allowing the mixture to stand.

Chemical substances used for the alkalization of the pH value of the liquid used for the alkali-treatment are not restricted to specific ones. Examples thereof include one or at least two members selected from the group consisting of alkaline organic compounds and alkaline inorganic compounds. Specific examples thereof are ammonia, ammonium salts, basic metal hydroxides (such as sodium hydroxide and potassium hydroxide), borates, phosphates, acetates, oxalates, citrates, tris-hydroxyaminomethane and mixtures of at least two of these substances.

Such chemical substances are used in a concentration, which never causes any modification or denaturation of human serum albumin.

If an SH group-containing compound is added to the alkaline solution used in the alkali-treatment, any uncorrected holding observed in an HSA molecule and/or between HSA molecules, or further between an HSA molecule and contaminants (they would mainly comprise proteins) and this permits the more effective conversion of the multimers into the monomers.

The SH group-containing compounds used in this treatment are not restricted to particular ones inasmuch as they are compounds each having an SH group, but preferred are low molecular compounds each having an SH group. Specific examples thereof include cysteine, cysteamine, cystamine and methionine, with cysteine being preferably used herein.

The amount of the SH group-containing compound to be added to the alkaline solution ranges from 0.1 to 50 mM, preferably 0.2 to 15 mM and more preferably 0.5 to 5 mM, for the concentration of rHSA falling within the range of from 1 to 100 mg/ml.

Then the HSA-containing solution is concentrated using an ultrafiltration membrane (whose molecular weight to be fractionated is set at 10000) and then the pH value of the solution is adjusted to a level in the proximity to the isoelectric point of the contaminants of the solution before the heat-treatment.

The heat-treatment is carried out at a temperature preferably ranging from 50 to 70° C., more preferably 55 to 60° C. and most preferably 60° C. The time required for the heat-treatment preferably ranges from 30 minutes to 5 hours and more preferably one hour.

The pH value during the heat-treatment is preferably one in the proximity to the isoelectric point of the contaminants. For instance, it preferably ranges from 4 to 7, more preferably 5 to 6 and most preferably 5.5 if yeast cells such as cells of *Saccharomyces cerevisiae* AH22 strain or mutant thereof are used as the human serum albumin-producing host cells.

Moreover, the concentration of the human serum albumin solution used in the heat-treatment is not restricted to any particular one inasmuch as the human serum albumin is completely dissolved in the solution. It preferably ranges from 10 to 250 mg/ml and more preferably 80 to 120 mg/ml.

The purity of human serum albumin achieved after the heat-treatment can be determined by the gel filtration HPLC analysis. For instance, this analysis may be carried out by loading a sample solution onto a column, TSKgel G300SW (available from Tosoh Corporation), eluting with 0.1 M $KH_2PO_4$/0.3 M NaCl buffer and then determining the absorbance of the resulting fractions observed at 280 nm. The human serum albumin solution prepared by the same procedures and free of any heat-treatment is used as a control.

Alternatively, a culture broth of yeast cells free of any human serum albumin-producing ability is roughly purified by the method similar to that used in the present invention, rabbits are immunized against the resulting product to give an anti-serum and any component originated from yeast cells present in the purified rHSA can then be determined according to the enzyme immunoassay technique (EIA technique) using the resulting anti-serum.

EXAMPLES

Preparation Example 1
Preparation of a Solution of Multimer-Containing Human Serum Albumin According to the method disclosed in TOKUHYO Hei 11-509525, rHSA was produced using yeast cells (*Saccharomyces cerevisiae*). This rHSA-containing culture broth was diluted with purified water to a total volume of about two times that of the original one and then the pH value of the diluted solution was adjusted to 4.5 using an aqueous acetic acid solution. Then the solution was loaded onto STREAMLINE SP Column (available from Amersham Pharmacia Biotech Company; diameter 60 cm×16 cm), which had been equilibrated with a 50 mM sodium acetate buffer solution (pH 4.5) containing 50 mM sodium chloride. Thereafter, the column was washed with a buffer solution identical to that used for equilibrating the column, followed by passing, through the column, a 50 mM phosphate buffer solution (pH 9.0) containing 300 mM sodium chloride to give rHSA-containing fractions.

Preparation Example 2
Alkali-Treatment of Cysteine-Containing Albumin Solution

To the resulting rHSA-containing fraction (10 ml), there were added 1 mM of cysteine and a 5% (w/v) dipotassium tetraborate solution (15 ml) to a final concentration of 3% (pH about 9.0), followed by allowing the resulting mixture to stand at room temperature for 5 hours. Then an aqueous acetic acid solution was added to the resulting solution to adjust the pH value of the solution to 7.0 and to thus complete the alkali-treatment.

Example 1
Heat-Treatment

Then the rHSA-containing aqueous solution was concentrated using an ultrafiltration membrane (available from Zartrius Company) having a fractionated molecular weight of 10000 to an rHSA concentration of about 100 mg/ml and simultaneously, the medium of the aqueous solution was replaced with a 50 mM phosphate buffer (pH 5.5) containing 5 mM sodium caprylate. The resulting rHSA solution was then heat-treated at 60° C. for one hour. Subsequently, the solution was cooled down to room temperature and precipitates formed were removed through centrifugation to thus recover the supernatant.

Test Example 1
Gel Filtration HPLC Analysis

The foregoing supernatant (0.2 ml) was loaded onto a TSKgel G300SW (available from Tosoh Corporation) column (diameter 0.75 cm×30 cm) equilibrated with 0.1 M $KH_2PO_4$/0.3 M NaCl buffer, the column was eluted with the same buffer and the absorbance of the resulting fraction was determined at a wavelength of 280 nm. The human serum albumin solution prepared by the same procedures and free of any heat-treatment was used as a control. The results of the analysis are plotted on FIG. 1.

Test Example 2
Analysis of Components Originated from Yeast Cells

A culture broth of yeast cells free of any human serum albumin-producing ability was roughly purified by the method similar to that used in the present invention, rabbits were immunized against the resulting product to give an anti-serum and an ELISA measurement system was constructed according to the usual method using the resulting anti-serum to thus determine any component originated from yeast cells present in the HSA-containing solution obtained by the method of the present invention. The results thus obtained are summarized in the following Table 1.

TABLE 1

| Sample | Amt. of Proteins/1 g of rHSA (μg) | Clearance |
|---|---|---|
| Before the Heat-Treatment | 1140 | |
| After the Heat-Treatment | 194 | 5.9 |

Industrial Applicability

According to the present invention, a human serum albumin solution containing proteinaceous contaminants originated from host cells is heat-treated at a pH value in the proximity to the isoelectric point of the proteinaceous contaminants to simply and effectively remove the proteinaceous contaminants from the human serum albumin solution.

Moreover, the present invention permits the preparation of high purity human serum albumin having a low content of substances originated from host cells, which may become a cause of side effects such as allergy observed when the human serum albumin is administered to the human. The present invention can be used in combination with other purification methods to further improve the purity of human serum albumin.

What is claimed is:
1. A method for preparing recombinant human serum albumin (HSA) from yeast, comprising:
   (1) subjecting HSA-containing fractions to an alkali-treatment at a pH value ranging from 8 to 11, at a temperature ranging from 0 to 60° C. and for a time of at least 15 minutes to convert multimers of recombinant human serum albumin into monomers, followed by

(2) heat-treating at a pH value in the proximity of the isoelectric point of yeast contaminants, at a temperature ranging from 50 to 70° C., at a pH of 5 to 6, and for a time ranging from 30 minutes to 5 hours.

2. The method of claim 1, wherein the subjecting is conducted at pH 9.0, at room temperature for 5 hours, and the heat-treating is conducted at pH 5.5, at 60° C. for 1 hour.

3. The method of claim 1, wherein (1) is conducted at a pH of 8.5 to 9.5.

4. The method of claim 1, wherein (1) is conducted for a time of not less than 3 hours.

5. The method of claim 1, wherein (1) is conducted at 25° C.

6. The method of claim 1, wherein (2) is conducted at a pH of 5.5.

7. The method of claim 1, wherein (2) is conducted at a temperature of 55 to 60° C.

8. The method of claim 1, wherein (2) is conducted at a temperature of 60° C.

9. The method of claim 1, wherein (2) is conducted for one hour.

10. A method for preparing recombinant human serum albumin from yeast, comprising:

(1) subjecting a culture broth of human serum albumin-producing yeast to cation exchange column chromatography, wherein the recombinant human serum albumin is adsorbed to and then eluted from the column, (2) subjecting the eluate to an alkali-treatment at a pH value ranging from 8 to 11, at a temperature ranging from 0 to 60° C. and for a time of at least 15 minutes, to convert the multimers of the recombinant human serum albumin into monomers, (3) concentrating the recombinant human serum albumin-containing solution by ultrafiltration, and (4) heat-treating the concentrate at a pH of 5 to 6.

11. The method of claim 10, wherein (2) is conducted at pH 9.0, at room temperature for 5 hours, and (4) is conducted at pH 5.5, at 60° C. for 1 hour.

12. The method of claim 10, wherein (2) is conducted at a pH of 8.5 to 9.5.

13. The method of claim 10, wherein (2) is conducted for a time of not less than 3 hours.

14. The method of claim 10, wherein (2) is conducted at 25° C.

15. The method of claim 10, wherein (4) is conducted at a pH of 5.5.

16. The method of claim 10, wherein (4) is conducted at a temperature of 55 to 60° C.

17. The method of claim 10, wherein (4) is conducted at a temperature of 60° C.

18. The method of claim 10, wherein (4) is conducted for one hour.

* * * * *